United States Patent
Chiu et al.

(10) Patent No.: US 8,697,121 B2
(45) Date of Patent: Apr. 15, 2014

(54) SPECTRALLY TUNABLE PHOTOLYSIS OF A CAPSULE CONTAINING AN ACTIVE MATERIAL

(75) Inventors: Daniel T. Chiu, Seattle, WA (US); Kimberly A. Dendramis, Seattle, WA (US); Peter B. Allen, Seattle, WA (US); Philip J. Reid, Seattle, WA (US)

(73) Assignee: Unviersity of Washington, Seattle, WA (US)

( * ) Notice: Subject to any disclaimer, the term of this patent is extended or adjusted under 35 U.S.C. 154(b) by 1817 days.

(21) Appl. No.: 11/925,480

(22) Filed: Oct. 26, 2007

(65) Prior Publication Data

US 2008/0283385 A1 Nov. 20, 2008

Related U.S. Application Data (60) Provisional application No. 60/863,016, filed on Oct. 26, 2006.

(51) Int. Cl.
*A61K 9/50* (2006.01)

(52) U.S. Cl.
USPC .......................... 424/452; 424/489; 424/490

(58) Field of Classification Search
CPC .................... A61K 9/16; A61K 2201/023
USPC .......................... 424/489–495, 452
See application file for complete search history.

(56) References Cited

U.S. PATENT DOCUMENTS

| | | | | |
|---|---|---|---|---|
| 3,301,439 A | * | 1/1967 | Kosar et al. | 222/52 |
| 5,912,257 A | * | 6/1999 | Prasad et al. | 514/356 |
| 2003/0191458 A1 | * | 10/2003 | Diamond et al. | 606/14 |
| 2004/0012872 A1 | * | 1/2004 | Fleming et al. | 359/885 |

OTHER PUBLICATIONS

Momotake, A., et al., "The Nitrodibenzofuran Chromophore: A New Caging Group for Ultra-Efficient Photolysis in Living Cells," Nature Methods 3(1):35-40, Jan. 2006.
Sun, B., et al., "Layered Polyelectrolyte-Silica Coating for Nanocapsules," Langmuir 21(23):10763-10769, Nov. 8, 2005.
Sun, B., and D.T. Chiu, "Determination of the Encapsulation Efficiency of Individual Vesicles Using Single-Vesicle Photolysis and Confocal Single-Molecule Detection," Analytical Chemistry 77(9):2770-2776, May 1, 2005.
Sun, B. et al., "Fast Initiation of Chemical Reactions with Laser-Induced Breakdown of a Nanoscale Partition," Langmuir 20(22):9437-9440, Oct. 26, 2004.
Sun, B., and D.T. Chiu, "Synthesis, Loading, and Application of Individual Nanocapsules for Probing Single-Cell Signaling," Langmuir 20(11):4614-4620, May 25, 2004.
Sun, B., and D.T. Chiu, "Spatially and Temporally Resolved Delivery of Stimuli to Single Cells," Journal of the American Chemical Society 125(13):3702-3703, Apr. 2, 2003.

* cited by examiner

*Primary Examiner* — Michael G Hartley
*Assistant Examiner* — Micah-Paul Young
(74) *Attorney, Agent, or Firm* — Christensen O'Connor Johnson Kindness PLLC (57) ABSTRACT

Capsules that include a shell, a sensitizer, and an active material. Methods for using the capsules to spatiotemporally deliver active material. Representative shells include vesicles, polymers, and inorganic materials. Representative active materials include small molecules and proteins.

20 Claims, 10 Drawing Sheets

SPECTRALLY TUNABLE PHOTOLYSIS OF A CAPSULE CONTAINING AN ACTIVE MATERIAL

CROSS-REFERENCE TO RELATED APPLICATION

This application claims the benefit of U.S. Provisional Application No. 60/863,016, filed Oct. 26, 2006, expressly incorporated herein by reference in its entirety.

STATEMENT OF GOVERNMENT LICENSE RIGHTS

This invention was made with U.S. government support under grant R21 AG 29574 awarded by the National Institutes of Health. The U.S. government has certain rights in the invention.

BACKGROUND OF THE INVENTION

High-resolution imaging methods are available for visualizing the spatial distribution of proteins and receptors on cell membranes, but these techniques do not provide functional information with regard to the activities of these proteins. Techniques capable of probing the functions of membrane proteins with high spatial and temporal resolution are limited, and much effort has been spent to develop such capabilities. The most notable and promising of these methods is the two-photon photolysis of photoactivable or "caged" molecules. Taking advantage of the nonlinear optical property of two-photon excitation, this technique can create a spatially focused un-caging volume that measures only a few hundred nanometers in width and height, as dictated by the far-field diffraction limit and the quadratic dependence of excitation on laser power. The availability of such a spatially and temporally selective method for probing cellular function and signaling dynamics is critical to understanding complex cellular and neuronal systems.

Despite the versatility offered by caged molecules, this approach is highly dependent on the availability of suitable photoactivable materials. The use of conventional chemically caged compounds suffers from a number of chemical drawbacks: (1) the design and synthesis of a suitable caged molecule is complex and time consuming, (2) the caging of large bioactive molecules such as peptides and proteins (e.g., cytokines) is difficult if at all possible, and (3) the un-caging of multiple stimuli simultaneously (e.g. for studying interactions among multiple signaling pathways) is often cumbersome. Because of these constraints, there are only a small number of caged molecules that have been developed over the past decades and an alternative technique for spatiotemporally delivering a stimulus to a biological system is needed.

SUMMARY OF THE INVENTION

The present invention provides capsules capable of releasing an active material upon photolysis aided by a sensitizer. The invention also provides methods for releasing an active material from a capsule and methods for delivering an active material to a cell using a capsule.

In one aspect, the invention provides a capsule for storing and releasing an active material. In one embodiment, the capsule includes a shell, composed of a shell material; a sensitizer having an absorbance wavelength from about 600 nm to about 1500 nm; and an active material.

In one aspect, the invention provides a capsule with multi-photon sensitizer molecules and an active material. In one embodiment, the capsule includes a shell composed of a shell material; a multi-photon sensitizer; and an active material.

In one aspect, the invention provides a method for releasing an active material from a capsule, including exposing a capsule to light having a wavelength from about 600 nm to about 1500 nm; where the capsule includes a shell composed of a shell material, a sensitizer, and an active material; and where the sensitizer has an absorbance wavelength overlapping the wavelength of light.

In one aspect, the invention provides a method for releasing an active material from a capsule. In one embodiment, the method includes exposing a capsule to a wavelength of light, where the capsule includes: a shell composed of a shell material, a multi-photon sensitizer having a multi-photon absorbance wavelength, and an active material; and where the multi-photon absorbance wavelength of the multi-photon sensitizer has sufficient overlap with the wavelength of light so as to achieve multi-photon excitation of the sensitizer.

In one aspect, the invention provides a method for delivering an active material to a cell, including exposing a capsule to light having a wavelength from about 600 nm to about 1500 nm; where the capsule includes a shell composed of a shell material, a sensitizer, and an active material; where the sensitizer has an absorbance wavelength overlapping the wavelength of light; and where the capsule is in proximity to a cell sufficient to deliver an effective amount of the active material to the cell.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE INVENTION

The present invention provides capsules capable of releasing an active material upon photolysis aided by a sensitizer. The invention also provides methods for releasing an active material from a capsule and methods for delivering an active material to a cell using a capsule. The capsules of the invention include a shell made of a shell material, a sensitizer, and an active material to be delivered to a target upon photolysis of the shell. The photolysis of the shell is facilitated by the sensitizer, which is excited by low-energy (i.e., red visible or infrared) light that initiates photolysis through energy transfer to the shell. Upon photolysis of the shell, the shell is fractured and the active material stored within the shell is released. An exemplary use for the capsules and methods of the invention is in a biological system, where the active material may be a therapeutic agent that is delivered to a precise location in a human body and released by photolysis via low-energy light.

In one aspect, the invention provides a capsule for storing and releasing an active material. In one embodiment, the capsule includes a shell, composed of a shell material; a sensitizer having an absorbance wavelength from about 600 nm to about 1500 nm; and an active material.

As used herein, the term "sensitizer" refers to any type of molecule that absorbs light and upon absorbing the light reaches an excited energetic state that transfers energy to the shell so as to initiate photolysis of the shell material. The excited state is typically the result of excitement from a ground electronic state to an excited electronic state. The sensitizer can absorb a single photon of light or multiple photons of light (e.g., two-photon and three-photon absorbance). In one embodiment, the sensitizer is capable of one-, two-, or three-photon excitation. The term "multi-photon sensitizer" refers to a sensitizer that is capable of two-photon, three-photon, or higher-order photon absorption. A single sensitizer may be capable of one- and multi-photon absorption. When a sensitizer absorbs a photon of light, the photon will either create an excited state by itself, such as is the case for one-photon excitation, or multiple photons may be needed to create the excited state, such as in two-photon excitation. While the peak absorbance of a multiple photon excitation may be in the ultraviolet (UV) or high-energy visible range of light, the absorbance events of the present invention are typically between 600 nm visible light and higher, with a typical range for one-photon absorbance between 600 nm and 1500 nm light. As used herein, the terms "high energy" and "short wavelength" are synonymous and refer to wavelengths of light shorter than 600 nm. High-energy wavelengths include green to UV wavelengths. As used herein, "low energy" and "long wavelength" refer to visible red light and near infrared (NIR) wavelengths, and "red-shifting" refers to moving to a longer wavelength.

In one embodiment, the sensitizer absorbance wavelength is a one-photon absorbance from about 600 nm to about 700 nm. In one embodiment, the sensitizer absorbance wavelength is a two-photon absorbance from about 700 nm to about 1500 nm. Multi-photon sensitizers can be characterized by a peak absorbance, which is the wavelength of the fully excited state, or the multi-photon absorbance, which is the wavelength of the individual photons used to create the excited state. Thus, a two-photon sensitizer with a peak absorbance of 365 nm will have a fractional absorbance of near 365×2 or 730 nm. There is a range of wavelengths that will satisfy the two-photon absorbance condition, however, and so an exemplary two-photon sensitizer may have a two-photon absorbance at 730 nm but the peak absorption may be at 365 nm plus or minus about 50 nm. The specific wavelengths at which multi-photon sensitizers useful in the invention have multi-photon absorbance is not important, so long as the sensitizer is sufficiently energetically excited so as to induce photolysis of the shell material.

Representative two-photon sensitizers useful in the invention have peak two-photon absorbance from about 300 nm to about 800 nm. Because two-photon absorbance creates a higher energy excited state relative to a similar one-photon absorbance at the same wavelength, further red-shifted wavelengths of light can be used to induce photolysis. Additionally, the high absorption efficiencies of two-photon sensitizers will increase the efficiency of energy transfer from light source (e.g., laser) to shell, and thus the efficiency of photolysis. A more efficient photolysis system requires less light power and fewer sensitizer molecules.

In one embodiment, the sensitizer absorbance wavelength is from about 700 nm to about 1500 nm. In one embodiment, the sensitizer absorbance wavelength is from about 600 nm to about 1000 nm. In one embodiment, the sensitizer absorbance wavelength is from about 700 nm to about 1000 nm.

Given the broad range of potential materials for the invention, there is a similarly broad range of possible sensitizer concentrations in the capsule. Photolysis results when a minimum amount of energy is transferred to the shell material. The laser/sensitizer system can be adjusted to achieve that amount of energy. The minimum concentration of sensitizer needed in capsules of the invention is a product of the wavelength and power of light used, the shell material, and the sensitizer efficiency. A smaller concentration of sensitizer is needed if the absorbance efficiency is high (i.e., a high ratio of light absorbed versus light irradiated). The sensitizer concentration can be calculated as a component of the shell (e.g., as mole % or weight % of materials in the shell). Additionally, the sensitizer can be independent of the shell material when it is attached to the surface of the shell or contained in the interior volume of the shell. In one embodiment, the sensitizer is in the shell or attached to its surface. Photolysis may still be possible with a low concentration of sensitizer (e.g., ~1 mol % of the shell) if the absorbance efficiency and/or laser power is high.

In one embodiment, the sensitizer comprises from about 1 to about 20 percent of the shell as calculated by total mole percentage of the shell. In one embodiment, the sensitizer comprises from about 10 to about 20 percent of the shell as calculated by total mole percentage of the shell. In one embodiment, the sensitizer comprises from about 1 to about 5 percent of the shell as calculated by total mole percentage of the shell.

The use of low-energy light to photolyze capsules of the invention makes for compatibility with biological systems. Most biological tissue is transparent at wavelengths near the visible/NIR transition, whereas higher energy (e.g., UV light) is absorptive. By using biologically transparent wavelengths to photolyze capsules of the invention, the capsules can be used with living organisms without harming tissue, thus making the present invention useful for delivering therapeutic and diagnostic biological applications. Another advantage of using lower energy light is that it will penetrate deeper through tissue in comparison to non-red visible and UV wavelengths. Finally, there is low auto-fluorescence background from cells and tissues in the red/infrared wavelength region.

Sensitizers can be incorporated into the shells of capsules formed from non-cross linked polymers, crosslinked polymers, lipids, anionic lipids, crosslinkable synthetic lipids, block copolymers, inorganic capsules, and combinations thereof. A wide variety of sensitizers with high absorption cross-sections (both fluorescent and non-fluorescent), can be incorporated into the shells of the capsules to allow for spectrally tunable photolysis. In addition, these sensitizers can be incorporated onto the surface of the shell or interior of the capsule. Typical sensitizers useful in capsules of the invention include carbocyanine-based dyes, rhodamine-based dyes, fluorescein-based dyes, various non-fluorescent dyes, neutral dyes, zwitterionic dyes, positively-charged dyes, negatively-charged dyes, reactive dyes, tagged dyes that contain an antibody, and combinations thereof. In one embodiment, the sensitizer is 1,1'-dioctadecyl-3,3,3',3',-tetramethylindodicarbocyanine, 4-chlorobenzenesulfonate salt (DiB); 1,1'-dioctadecyl-3,3,3',3',-tetramethylindotricarbocyanine iodide (DiR); or 1,1'-dioctadecyl-3,3,3',3',-tetramethylindocarbocyanine perchlorate (DiI). Other exemplary sensitizers include 5,5'-dibromo-1,1'-dioctadecyl-3,3,3',3'-tetramethylindocarbocyanine perchlorate; 4-(4-(didecylamino)styryl)-N-methylpyridinium iodide; 1,1'-didodecyl-3,3,3',3'-tetramethylindocarbocyanine perchlorate; 4-(4-(dihexadecylamino)styryl)-N-methylpyridinium iodide; 3,3'-dihexadecyloxacarbocyanine perchlorate; 1,1'-dihexadecyl-3,3,3',3'-tetramethylindocarbocyanine perchlorate; 4-(4-(dilinoleylamino)styryl)-N-methylpyridinium 4-chlorobenzenesulfonate; 4-(4-(dilinoleylamino)styryl)-N-methylpyridinium iodide; 3,3'-dilinoleyloxacarbocyanine perchlorate; 1,1'-dilinoleyl-3,3,3',3'-tetramethylindocarbocyanine, 4-chlorobenzenesulfonate; 1,1'-dilinoleyl-3,3,3',3'-tetramethylindocarbocyanine perchlorate 1,1'-dioctadecyl-5,5'-diphenyl-3,3,3',3'-tetramethylindocarbocyanine chloride; 3,3'-dioctadecyloxacarbocyanine perchlorate (DiO); 1,1'-dioctadecyl-3,3,3',3'-tetramethylindocarbocyanine-5,5'-disulfonic acid; 1,1'-dioctadecyl-3,3,3',3'-tetramethylindodicarbocyanine perchlorate; 1,1'-dioleyl-3,3,3',3'-tetramethylindocarbocyanine methanesulfonate; and antibody-tagged dyes manufactured by Invitrogen: Alexa Fluor 488, 514, 532, 546, 555, 568, 594, 610, 633, 635, 647, 660, 680, 700, and 750. Representative multi-photon sensitizers include two-photon sensitizers: DiI; rhodamine B; 3,4-Bis(decyloxy)-2,5-bis(benzothiazol-2-yl)thiophene; 2-Bromo-3,4-bis(decyloxy)-5-(benzothiazol-2-yl)thiophene; and 3,4,3',4'-Tetradecyloxy-5,5'-bis(benzothiazol-2-yl)-2,2'-bithiophene.

Examples of processes to incorporate the sensitizers into the shell of the capsules include integrating them into a lipid vesicle membrane through extrusion, or incorporation in polymer-based shells during interfacial polymerization using a layer-by-layer, charge-driven mechanism. The sensitizers may also be covalently linked to polymer molecules that form the shell, or they can be attached and incorporated into the shell via a non-covalent mechanism, such as spatial tapping, electrostatic, Van der Waals, hydrogen bonding, hydrophobic interactions, or combinations thereof. In the case of covalent linkages, the sensitizers may be designed to be part of the polymer molecules that form the shell of the capsule and are thus an integral part of the shell material.

When the sensitizer becomes excited, the excited-state energy of the sensitizer is then transferred to the shell material, thus inducing the photolysis of the shell material and causing the shell to fracture. Upon fracture of the shell, the capsule is effectively destroyed and the active material contained within the shell is released.

The shell encloses the active material and is made of at least a shell material, but may also incorporate the sensitizer and/or active material. The shell material will determine the amount of energy needed to initiate the photolysis reaction, and thus the amount and type of sensitizer, as well as the power of light (e.g., laser) needed.

In one embodiment, the shell defines an interior volume that contains the active material. As used herein, the term "interior volume" refers to the interior space formed by the shell of the capsule. The interior volume is typically filled with a (non-shell material) medium that includes an active material. The positioning of the elements of the capsule are primarily defined in relation to the shell, which typically forms the outer boundary of the capsule. The sensitizer may be located on the surface of the shell and attached by either covalent, ionic, or other attractive forces. The sensitizer may be incorporated into the shell material either as a non-bonded element of a mixture of materials that make up the shell, or as a covalently-bound element of the shell material. An exemplary embodiment of a covalently bound sensitizer is a copolymer with the shell material as the backbone of the polymer and the sensitizer as a pendant or grafted group to the main polymer backbone. The sensitizer may also be located within the interior volume of the shell.

In one embodiment, the shell material is a lipid, a polymer, or an inorganic material. The shell is typically made of one or more shell materials.

Representative lipids useful in the invention include natural lipids (such as phospholipids), synthetic lipids (such as 1,2-dioleoyl-sn-glycero-3-phosphocholine (DOPC); 1-palmitoyl-2-oleoyl-sn-glycero-3-phosphocholine (POPC); L-α-phosphatidylcholine (egg PC); 1,2-dioleoyl-3-trimethylammonium-propane (chloride salt) (DOTAP); 1,2-dipalmitoyl-sn-glycero-3-[phospho-rac-(1-glycerol)] (sodium salt) (DPPG); and 1,2-dipalmitoyl-sn-glycero-3-phosphoethanolamine (DPPE)), and crosslinkable lipids (such as 1,2-bis(10,12-tricosadiynoyl)-sn-glycero-3-phosphocholine (DiynePC) and 1,2-bis(10,12-tricosadiynoyl)-sn-glycero-3-phosphocholine (DC8,9PC)).

In one embodiment, the shell is a vesicle. A vesicle is a single or double layer of lipids arranged in a sphere-like structure. A polar functionality defines the outer surface when in an aqueous environment and a nonpolar functionality defines the interior (for a single-layer vesicle). An exemplary vesicle of the invention is a phospholipid vesicle. In one embodiment, the vesicle of the invention is a phosphatidyl choline vesicle.

Capsules of the present invention also include polymer shell materials. Any polymer material may be used in the invention as long as it is: 1) capable of forming a shell; 2) capable of incorporating a sensitizer into the shell (or on its surface or in the interior volume); and 3) the sensitizer is capable of transferring a sufficient amount of energy to the shell so as to cause photolysis of the shell material at wavelengths equal to or longer than 600 nm.

For a polymer to be capable of forming a shell, the polymer is capable of enclosing an active material to the extent that the active material is contained within the polymer shell. While some diffusion of the active material across the shell may occur, for a capsule of the invention to be effective in delivering an active material, an effective amount of the active material remains encapsulated immediately prior to photolysis.

A polymer is capable of incorporating a sensitizer into the shell if the sensitizer is able to be physically trapped or covalently, ionically, or otherwise bonded to the shell material. A sensitizer may simply be doped into a polymer (i.e., not chemically bound), the sensitizer may be a pendant group grafted onto a polymer chain (e.g., as part of a graft copolymer), or the sensitizer may be attached to the surface of the polymer shell or contained within the inner volume (i.e., encapsulated inside of the shell with the active material).

Representative polymers useful as shell materials of the invention include polystyrenes; poly(vinyl chloride); polyacrylonitrile; polyelectrolytes such as poly(sodium styrene sulfonate and poly(acrylic acid); silicones; fluoropolymers; polymethylmethacrylate; polydimethylsiloxane; polyethylene; polypropylene; polybutylene; polymethylpentene; polystyrene; polyurethane; polyvinyl chloride; polyarylate; polyarylsulfone; polycaprolactone; polyestercarbonate; polyimide; polyketone; polyphenylsulfone; polyphthalamide; polysulfone; polyamide; polyester; epoxy polymer; and combinations thereof. Block copolymers are also useful in the invention, and include di- and tri-block copolymers with the blocks independently selected from polystyrene, poly(acrylate), poly(methacrylate), polybutadiene, poly(oxirane), polylactone, polylactides, polyoxazoline, poly(vinyl pyridine), and polysiloxane.

Polymer capsules of the invention can be formed by a variety of methods, including self-assembly based processes, sacrificial processes, emulsion polymerization, extrusion, sonication, and evaporation. Other examples of methods are chemical, interfacial, radical, and photo-initiated polymerization.

Capsules of the present invention also include shells composed of inorganic materials. Any inorganic material may be used in the invention as long as it is: 1) capable of forming a shell; 2) capable of incorporating a sensitizer into the shell (or on its surface or in the interior volume); and 3) the sensitizer is capable of transferring a sufficient amount of energy to the shell so as to cause photolysis of the shell material at wavelengths equal to or longer than 600 nm. Exemplary inorganic shell materials include silica and metals. Silica, gold, and silver, are particularly well know to those skilled in the art as inorganic materials capable of forming shells that would be useful in the invention.

The shell need not be spherical, but may be any shape, including ellipsoids, triangles, cubes, and higher order polygons. Exemplary polymer shells of the invention may be made by templating, emulsion polymerization, or block co-polymerization.

In one embodiment, the capsule shell has a diameter of from about 10 nm to about 1000 nm. This distance is measured as the diameter of a sphere or as the opposing side-to-side measurement of a cube or higher order polygon.

In one embodiment, the shell further comprises a targeting agent. As used herein, the term "targeting agent" refers to a chemical functionality that can be attached to the surface of the capsule and has an affinity towards a second type of chemical functionality. Capsules can be constructed such that the surface of the shell is functionalized (either covalently or non-covalently) with cell-specific or tissue-specific molecules (such as antibodies and aptamers) that will cause the capsules to target and bind to specific cells or tissues (such as tumor cells) of interest. Shell materials can functionalized in many different ways, such as with polyethylene glycol (PEG) polymers; biotinylation; with amine terminals; or with carboxyl or succinimidyl ester groups. Exemplary targeting agents include a wide range of biological recognition molecules, including but not limited to antibodies, small molecules, proteins, carbohydrates, nucleic acids (e.g., DNA or RNA), aptamers, molecular beacons, and combinations thereof.

The purpose of the capsules and methods of the invention is to deliver an active material to a specific location and release it at a specific time. As used herein, the term "active material" refers to a broad range of materials that may be encapsulated in capsules of the invention and will have any type of diagnostic or therapeutic effect. Capsules useful in the invention encapsulate many different types of active materials, from small ions to proteins and nucleic acids (e.g., DNA or RNA). Exemplary active materials include, but are not limited to: metal ions (e.g., $Ca^{2+}$), carbachol, glutamate, $a\beta^4$, histamine, aptamer drugs, PNA, receptor agonists, receptor antagonists, neurotransmitters, neurotransmitter analogues, enzyme inhibitors, ion channel modulators, G-protein coupled receptor modulators, transport inhibitors, hormones, peptides, toxins, antibodies, pharmaceutical agents, chemicals, purinergics, cholinergics, serotonergics, dopaminergics, anesthetics, benzodiazepines, barbiturates, steroids, alcohols, metal cations, cannabinoids, cholecystokinins, cytokines, excitatory amino acids, GABAergics, gangliosides, histaminergics, melatonins, neuropeptides, neurotoxins, endothelins, nitric oxide compounds, opioids, sigma receptor ligands, somatostatins, tachykinins, angiotensins, bombesins, bradykinins, prostaglandins, and combinations thereof. In many cases, a select combinations of several active materials may be used. Thus, in one embodiment, capsules of the invention contain an active material that includes two or more active materials.

Figure 1:
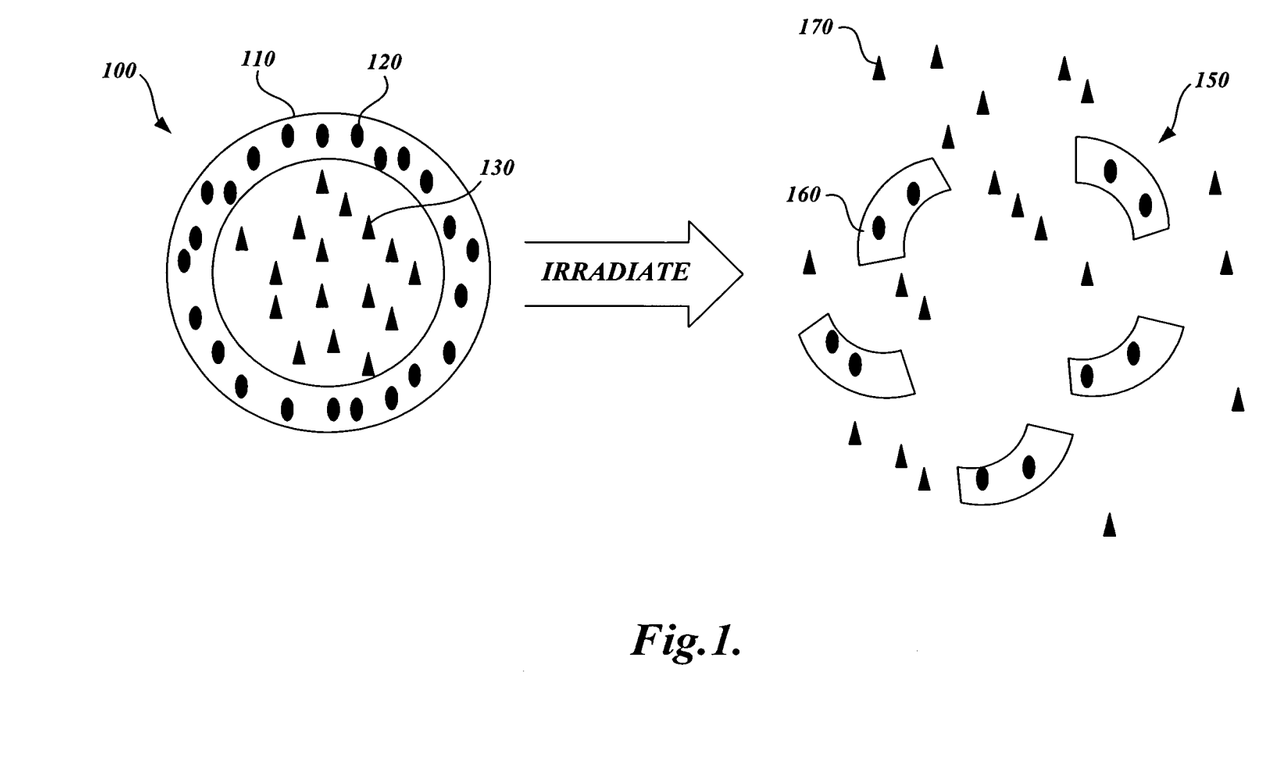
FIG. 1 schematically illustrates a representative method of the invention.

A representative capsule and method of the present invention is illustrated in FIG. 1. The capsule can be used to deliver an active material to a targeted location. The release of the active material is triggered by a wavelength of light that is spectrally tunable based on the absorbance characteristics of the sensitizer used to assist in the photolysis of the shell material. Referring to FIG. 1, the capsule 100 includes a shell material 110 that has incorporated sensitizers 120. Contained within the shell is an active material 130. External from the capsule is a laser or other light source to irradiate the capsule. Upon irradiation at a wavelength matched to the absorbance of the sensitizer, the shell material is photolyzed and the capsule is effectively destroyed. The fragmented capsule 150 includes a fractured shell 160 and released active material 170. Once the active material is released from the capsule upon irradiation, it will freely diffuse into the surrounding environment based on local conditions.

Breakdown (i.e., photolysis) of the shell material will release the active material. The length of time required before photolysis of the shell material is completed correlates to the duration of the laser pulse, the power of the laser, the mechanism of photolysis, and the photolysis efficiency of the material.

Figure 2:
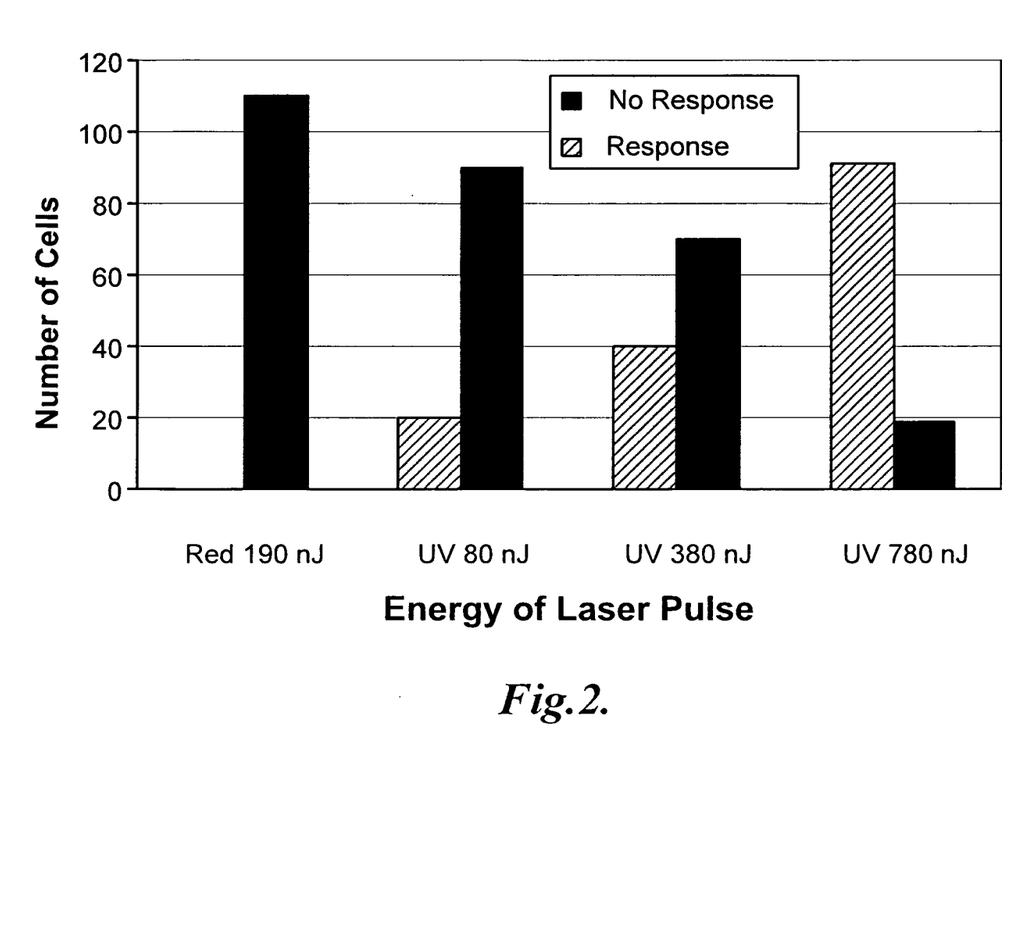
FIG. 2 graphically illustrates the effect of red and ultraviolet laser pulses on cells.

The cellular response to a single laser pulse across varying wavelengths of light and varying energy levels of laser pulse is illustrated in FIG. 2 and described in Example 1. In the invention, it is not desirable for cells to respond to the wavelength of light used to photolyze the capsules. The importance of using low-energy (e.g., red visible or infrared) light in the invention is illustrated in FIG. 2, where the cellular activity produced when ultraviolet wavelength laser light is directed at a cell is graphically illustrated. The "Red 190 nJ" bar on the far left of FIG. 2 illustrates a red laser pulse on a cell that shows no response to the light. As the wavelength of the laser is changed to the ultraviolet wavelength of 355 nm, even a significantly less powerful laser pulse will elicit a response from the cell, and as the power of the laser is increased to 380 nJ and 780 nJ, the cellular response increases.

Figure 3:
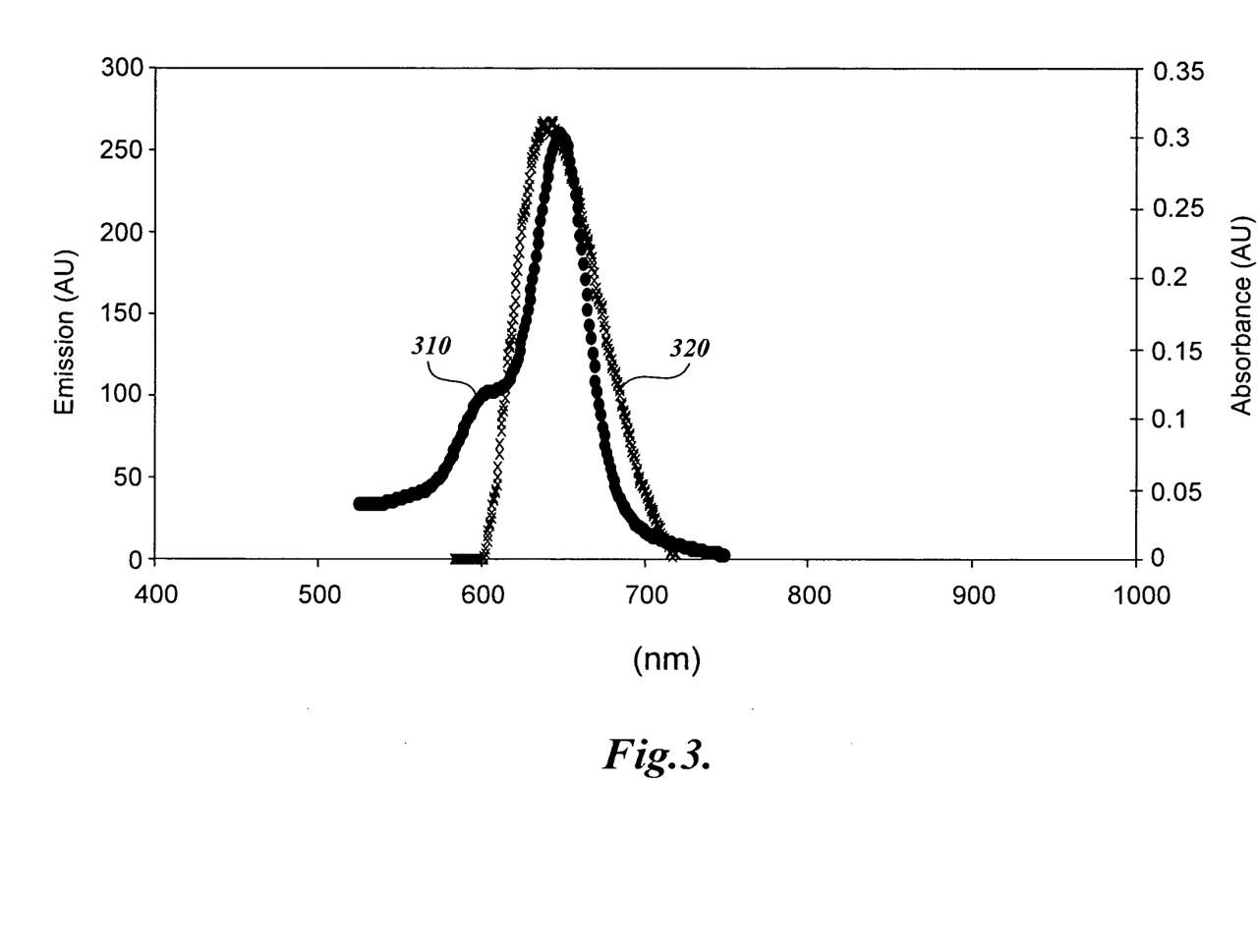
FIGS. 3, 3A, and 3B graphically illustrate the emission spectrum of a representative laser dye and sensitizer molecule useful in the invention.
Figure 3A:
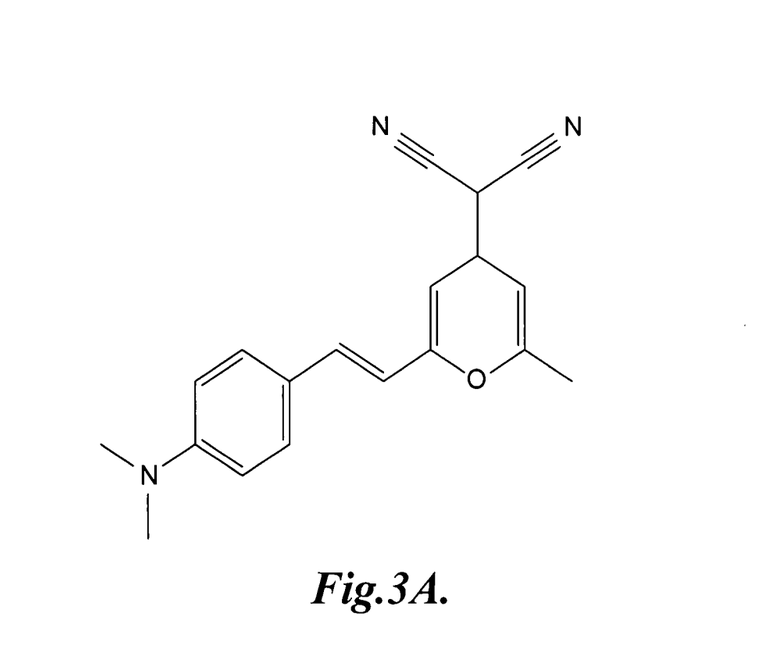
Figure 3B:
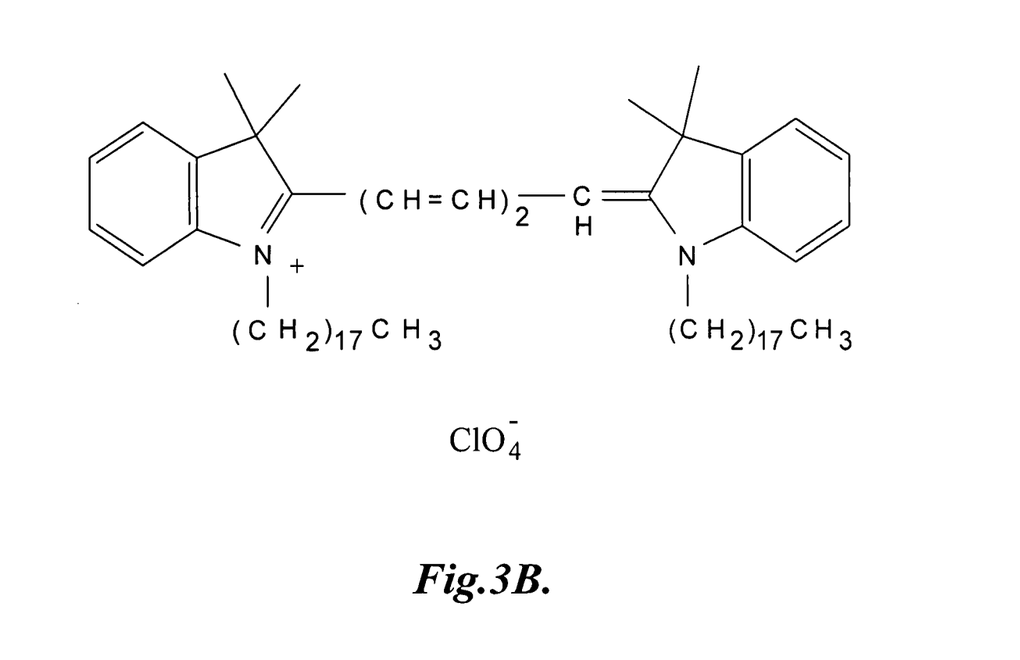
Figure 4:
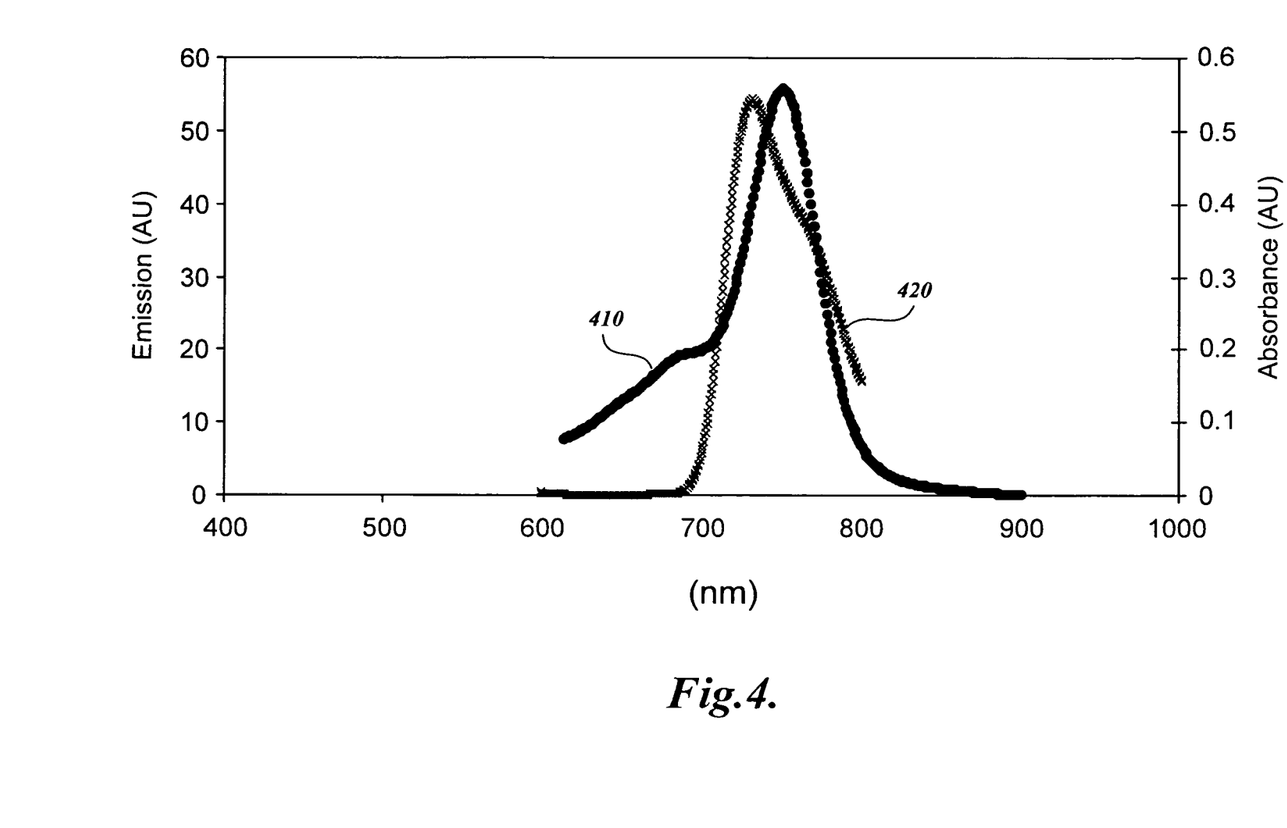
FIGS. 4, 4A, and 4B graphically illustrate the emission spectrum of a representative laser dye and sensitizer molecule useful in the invention.
Figure 4A:
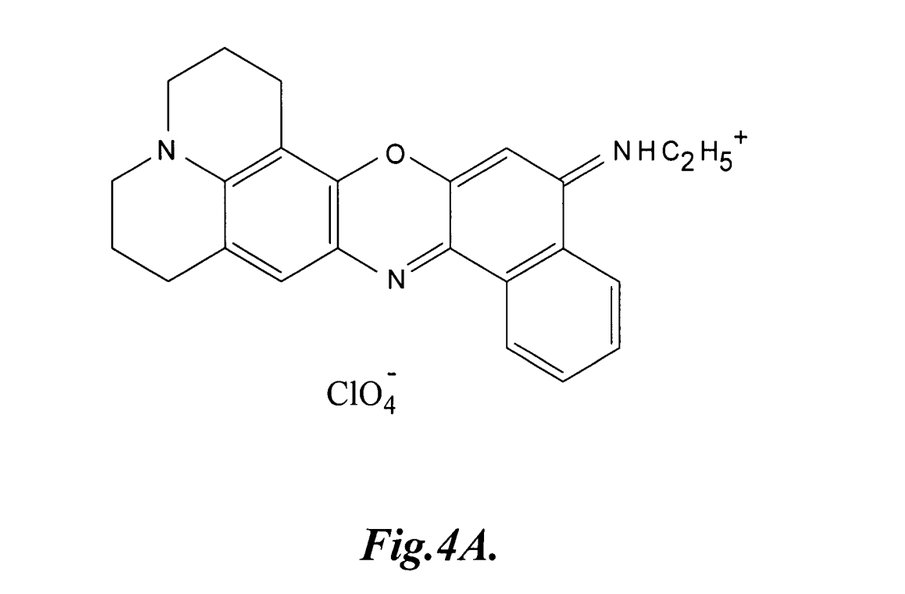
Figure 4B:
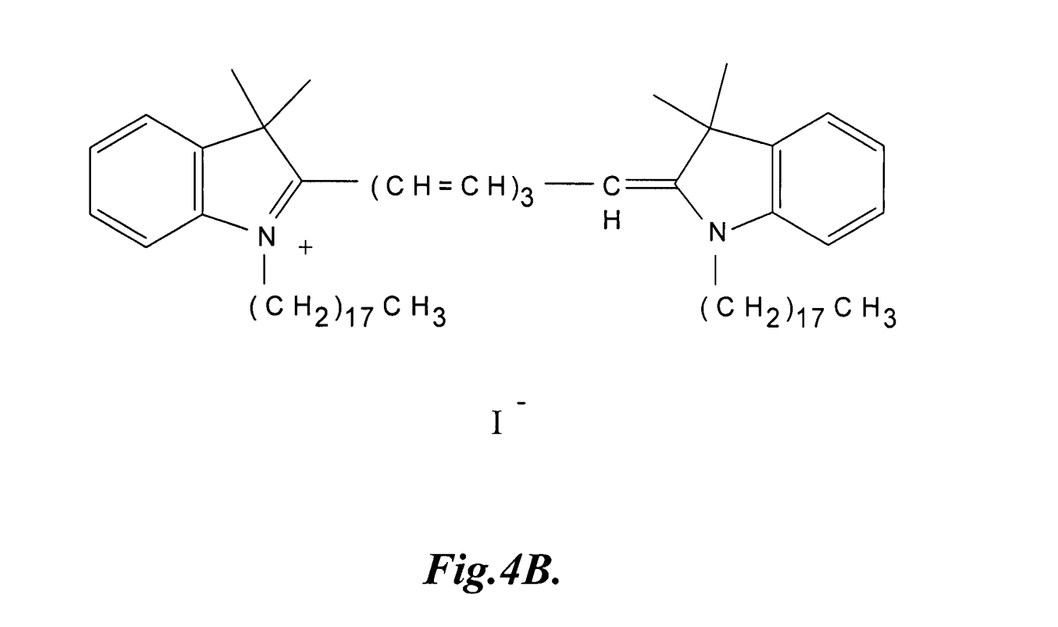

Representative sensitizers and dyes used to produce laser wavelengths are described in Example 2 and illustrated in FIGS. 3, 3A, 3B, 4, 4A, and 4B. FIG. 3 illustrates the absorbance spectrum 310 of the sensitizer DiD (as illustrated in FIG. 3B) and the emission spectrum 320 of the laser dye DCM (as illustrated in FIG. 3A). The overlap between the emission spectrum of the laser dye and the absorption of the sensitizer shows that the pair are optimal for generating a power transfer between the laser and the sensitizer. By matching the emission/absorbance, the ability of the sensitizer to become excited, transfer the excited energy state to the shell material, and initiate photolyzation is enhanced. By pairing an output laser wavelength with a sensitizer having a distinct absorbance spectrum, one skilled in the art can select a system that will produce an optimal absorbance by the sensitizer and, thus, optimal energy transfer between a laser and the shell so as to increase the probability of photolyzation. The laser output wavelength and sensitizer can be tuned to longer or shorter wavelengths based on the system in which they are used. As illustrated in FIG. 2, the use of red and infrared wavelengths of light are less destructive to cellular tissue and, thus, wavelengths between 600 nm and 1500 nm will produce results representative of the invention. FIG. 4 graphically illustrates the absorbance spectrum of a sensitizer 410 (DiR, as illustrated in FIG. 4B) being used in conjunction with a laser dye 420 (Oxazine 750, as illustrated in FIG. 4A), both of which are red-shifted from the laser/sensitizer system used to generate FIG. 3. By using a sensitizer that is able to absorb more strongly at a lower energy wavelength than the sensitizer (DiD) in FIG. 3, the laser/sensitizer system of FIG. 4 will further decrease the potentially harmful effects of the laser on biological systems.

Figure 5A:
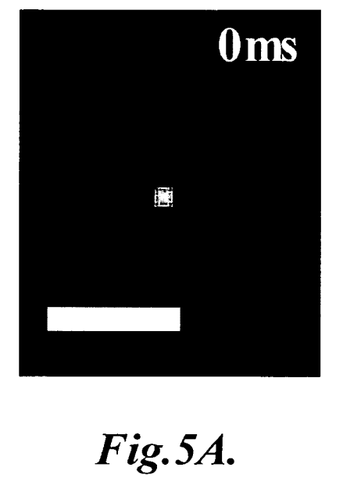
FIGS. 5A-5C illustrate the photolysis of a capsule by a laser.
Figure 5B:
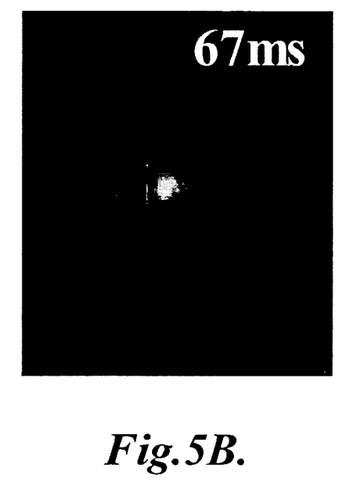
Figure 5C:
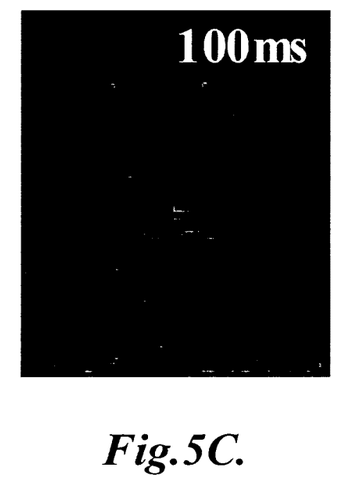

An example of the photolysis of a representative capsule of the invention is illustrated in FIGS. 5A-5C and described in Example 3. In FIG. 5A, a representative capsule of the invention is shown. The capsule is a vesicle that has the sensitizer DiD doped into the shell material, a phospholipid. In FIG. 5B, the results of photolysis are seen as the active material, a fluorescent material, is released from the vesicle after a red laser pulse is delivered to the vesicle. FIG. 5C illustrates the resulting diffusion of the active material upon the photolyzation and destruction of the capsule, as only a very faint fluorescent signal is detected, demonstrating that the active material has diffused away from the original location of the capsule. Example 3 further describes, and FIGS. 6A-6D, 7A-7D, and 8A-8D all illustrate, the photolysis of a representative capsule of the invention by a representative method of the invention. The capsule is loaded with an active material that will stimulate the cell and upon photolysis by red or infrared wavelength laser, the active material is released from the capsule and the active material diffuses to the nearby cell, thus stimulating a detectable cellular mechanism.

Light sources useful in the invention are capable of emitting a wavelength and power of light that will induce photolysis of a shell material via an appropriately paired sensitizer (i.e., good spectral overlap between emission/absorption). Exemplary light sources include pulsed and continuous wave lasers, flashlamps, and the output of an optical fiber coupled to an appropriate light source.

In one aspect, the invention provides capsules with multi-photon sensitizer molecules and an active material. In one embodiment, the capsule includes a shell, composed of a shell material; a multi-photon sensitizer; and an active material. In one embodiment, the multi-photon sensitizer is a two-photon sensitizer.

In one aspect, the invention includes a capsule having a shell defining an interior volume, where the shell is composed of a shell material and includes a plurality of sensitizers, each sensitizer having an absorbance in the range from about 600 nm to 1500 nm, and where the interior volume includes an active material.

In one aspect, the invention includes a vesicle, including an active material encapsulated by a lipid shell, where the shell includes a shell material and a plurality of sensitizers, each sensitizer having an absorbance in the range from about 600 nm to 1500 nm.

In one aspect, the invention provides a method for releasing an active material from a capsule, including exposing a capsule to light having a wavelength from about 600 nm to about 1500 nm; where the capsule includes a shell composed of a shell material, a sensitizer, and an active material; and where the sensitizer has an absorbance wavelength overlapping the wavelength of light. In one embodiment of the invention, the sensitizer is capable of one-, two-, or three-photon excitation.

In one embodiment, the sensitizer absorbance wavelength is from about 700 nm to about 1500 nm. In one embodiment, the sensitizer absorbance wavelength is from about 600 nm to about 1000 nm. In one embodiment, the sensitizer absorbance wavelength is from about 700 nm to about 1000 nm.

In one aspect, the invention provides a method for releasing an active material from a capsule. In one embodiment, the method includes exposing a capsule to a wavelength of light, where the capsule includes: a shell composed of a shell material, a multi-photon sensitizer having a multi-photon absorbance wavelength, and an active material; and where the multi-photon absorbance wavelength of the multi-photon sensitizer has sufficient overlap with the wavelength of light so as to achieve multi-photon excitation of the sensitizer. As used herein, the term "multi-photon excitation" refers to an excitation event in a sensitizer caused by two or more low-energy photons acting substantially simultaneously to create an excited state of greater energy than that contained in a single low-energy photon. A representative example of multi-photon excitation is two-photon absorption. In one embodiment, the multi-photon sensitizer is a two-photon sensitizer.

In one aspect, the invention provides a method for delivering an active material to a cell, including exposing a capsule to light having a wavelength from about 600 nm to about 1500 nm; where the capsule includes a shell composed of a shell material, a sensitizer, and an active material; where the sensitizer has an absorbance wavelength overlapping the wavelength of light; and where the capsule is in proximity to a cell sufficient to deliver an effective amount of the active material to the cell. Typically, the closer the capsule is to the cell the more active material will reach the cell, thus, in one embodiment the capsule is in physical contact with the cell. The effective amount of the active material will be determined by the application. Representative examples of an effective amount of active material would be an amount of an imaging molecule sufficient to facilitate imaging, or an amount of a therapeutic agent sufficient to produce an effect. The proximity required to deliver the active material will depend on the concentration and efficacy of the active material, as well as the diffusion of the local medium. Thus, in a similar medium and at similar amount of active material, a powerful therapeutic may be released further from the cell than a weaker one because, although a smaller amount of the powerful active material may reach the cell (due to a greater length for diffusion/dispersion), the effective therapy to the cell may be the same as that delivered by the closer, weaker active material.

In one embodiment of the invention, the sensitizer is capable of one-, two-, or three-photon excitation. In one embodiment, the sensitizer absorbance wavelength is from about 700 nm to about 1500 nm. In one embodiment, the sensitizer absorbance wavelength is from about 600 nm to about 1000 nm. In one embodiment, the sensitizer absorbance wavelength is from about 700 nm to about 1000 nm.

Because of the broad potential of the present invention as a delivery vehicle for any number of active materials, the types of cells that may be used in the method of the invention are limited only by the active materials used. In Example 3 (and illustrated in FIGS. 7A-7D), a Chinese Hamster Ovary (CHO) cell was used in the method of the invention, but any type of cell may be used. Exemplary cell types include: CHO-K1, PC 12, NG108-15, HEK-293, HeLa, MCF7, HT-29, SK-BR-3, SK-HEP-1, A549, 10P12, CHO DP12, Ch-27, ES-D3, retinal cells, and tissue slices (such as from rat brains).

Additional applications of the invention are discussed in Example 4. Representative applications of the invention include biological imaging, the protection and controlled release of pharmacologically active substances, and gene therapy.

The following examples are provided for the purpose of illustrating, not limiting, the invention.

EXAMPLES

Example 1

Cell Response to Red and Ultraviolet Lasers

One of the advantages of using lower energy (e.g., red) light for photolysis of capsules is the lack of a detrimental effect on cells by the laser pulse. FIG. 2 illustrates the response of Chinese Hamster Ovary (CHO) cells after being irradiated by a single laser pulse using 645 nm (red light) and 355 nm (UV) pulses. For readout of cellular response to the lasers, calcium imaging was employed. The cell was loaded with Fluo3, a calcium sensitive dye. Calcium mediates signaling pathways for cellular repair and apotosis, and thus its level acts as a good reporter of cell stress. FIG. 2 is a histogram that summarizes the results. No cellular response was observed (i.e. no increase in intracellular levels of calcium) for the 645 nm laser pulse at 190 nJ of power. In contrast, the 355 nm UV laser pulses readily illicit cellular response and cause cell stress, with an increasing number of cells responding as the pulse energy was increased from 80 nJ to 380 nJ to 780 nJ.

Example 2

Representative Laser Dye/Sensitizer Systems

Initiation of photolysis at a desired wavelength requires capsules sensitized to strongly absorbs at the wavelength of the laser used. FIG. 3 illustrate the absorbance spectrum 310 of the sensitizer DiD and the emission spectrum 320 of the laser dye 4-dicyanomethylene-2-methyl-6-(p(dimethylamino)styryl)-4H-pyran (DCM), used to produce nanosecond (~3 ns) pulses of 645 nm light. The output of a nitrogen laser was used to pump the dye laser. The emission of DCM has excellent spectral overlap with the absorption of DiD. FIG. 3A illustrates the molecular structure of laser dye DCM and FIG. 3B illustrates the molecular structure of sensitizer DiD. FIG. 4 illustrate the absorbance spectrum 410 of the sensitizer DiR and the emission spectrum 420 of the laser dye Oxazine 750, used to produce nanosecond (~3 ns) pulses of 750 nm light. The output of a nitrogen laser was used to pump the dye laser. The emission of Oxazine 750 has excellent spectral overlap with the absorption of DiR. FIG. 4A illustrates the molecular structure of laser dye Oxazine 750 and FIG. 4B illustrates the molecular structure of sensitizer DiR. The use of sensitizers DiR and DiD illustrate the wavelength tunability of the capsule and methods of the present invention.

Example 3

Photolysis of Capsules

In this example, three systems illustrating successful photolysis and active material release from phospholipids vesicles are presented. The scale bar on each micrograph is 3 microns. Each figure frame displays a time in milliseconds (ms) and the irradiation event is immediately after time=0 ms.

The capsules of this example have shells composed of a phosphatidyl choline shell material and a sensitizer. The sensitizer is doped into (i.e., not covalently bonded to) the shell material during formation of the shell. An active material is then loaded into the capsules via a liquid diffusion process.

Representative capsules of the invention are formed by combining the shell material (i.e., lipid) and the sensitizer in chloroform. The resulting shells (vesicles) are dried under nitrogen and then rehydrated in a buffer (typically near pH 7.0). Representative buffers include "Biological Buffer" (pH=7.4), phosphate buffer (pH=6.8), and HEPES buffer (pH=8.0). Uniform shell size is achieved by passing the dispersed shells through an extruder (such as those made by Avanti Polar Lipids Inc.). Depending on the pore size of the membrane used for extrusion, a mixture of unilamellar and multilamellar vesicles in the size range of 100 nm-1000 nm are produced. Additionally, vesicles can be formed by sonication (for smaller vesicles, e.g., less than 100 nm) or by rotovap (resulting in unilamellar vesicles larger than 1000 nm).

FIGS. 5A-5C depict the photolysis of a single 400 nm (diameter) capsule with 645 nm light. The capsule used was a vesicle made from phosphatidyl choline doped with 13 mol % DiD. For visualization in fluorescence, 50 mM carboxyfluorescein was encapsulated within the vesicle as the active material. Upon photolysis, the encapsulated carboxyfluorescein was released from the vesicle (FIG. 5B) and then rapidly diffused away from the point of photolysis (FIG. 5C).

Figure 6A:
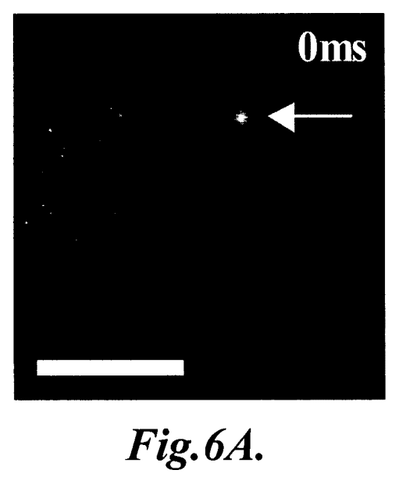
FIGS. 6A-6D illustrate the stimulation of a cell by one-photon photolysis of a capsule containing an active material.
Figure 6B:
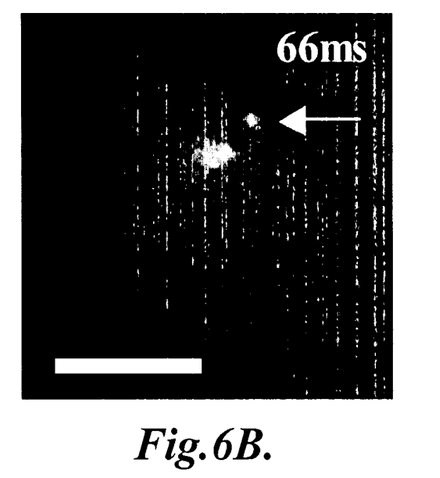
Figure 6C:
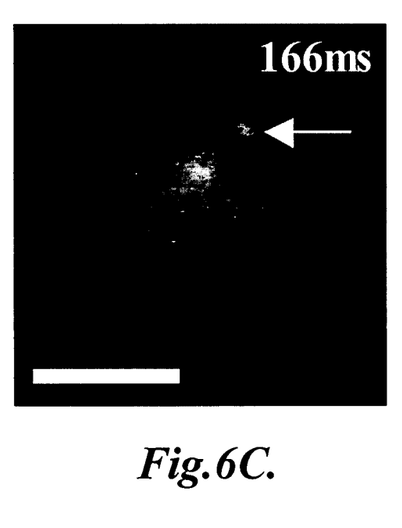
Figure 6D:
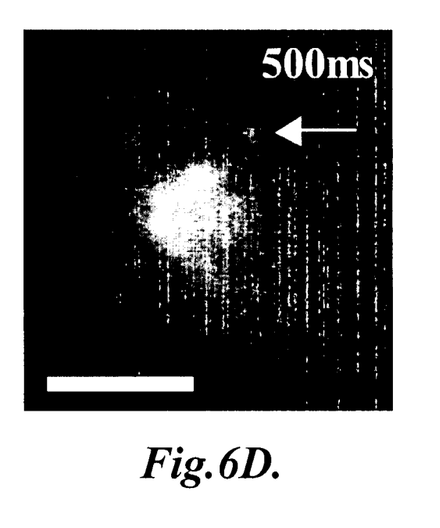

The method of the invention was used to achieve spatiotemporally resolved stimulation of cells, as illustrated in FIGS. 6A-6D, using 645 nm light. The capsules used were phosphatidyl choline vesicles loaded with carbachol. CHO-M1 cells were used that stably express the M1 muscarinic receptor. When carbachol binds to the M1 receptor, a G-protein is activated, which in turn hydrolyzes phosphoinositide, producing $IP_3$. The presence of $IP_3$ causes an increase in the intracellular level of calcium ions that can be visualize with Fluo3. To achieve photolysis of capsules at 645 nm, the shell of the vesicle was doped with 13 mol % DiD. For visualization of the vesicle in fluorescence, a membrane dye (3,3'-dioctadecyloxacarbocyanine perchlorate) was also used in the capsule shell. FIGS. 6A-6D show the results of a typical experiment, in which a single 400 nm vesicle (arrow), non-specifically attached to a single cell, was photolyzed. Prior to photolysis (time 0 ms, FIG. 6A), the intracellular calcium level was low and the cell was not visible in fluorescence. After photolysis and the release of the active material (carbachol), intracellular calcium increases and propagates across the cell (66 ms to 500 ms; FIGS. 6B-6D).

Figure 7A:
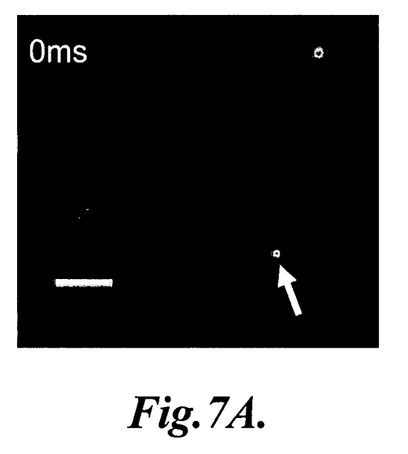
FIGS. 7A-7D illustrate the stimulation of a cell by two-photon photolysis of a capsule containing an active material.
Figure 7B:
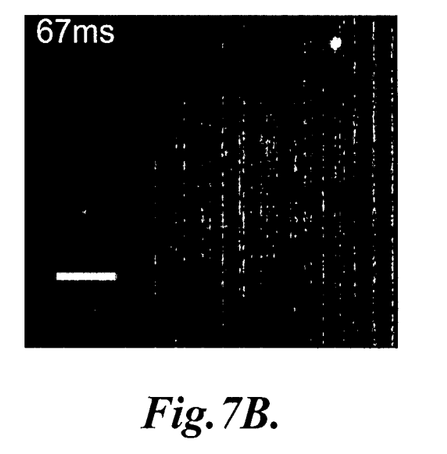
Figure 7C:
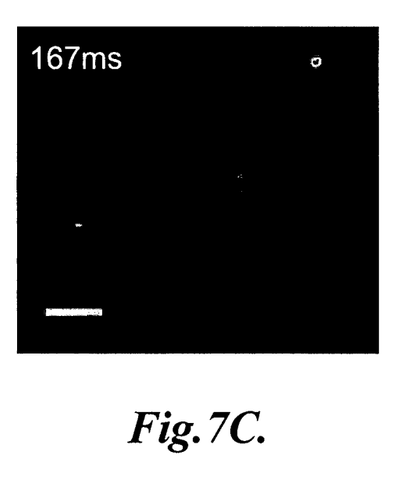
Figure 7D:
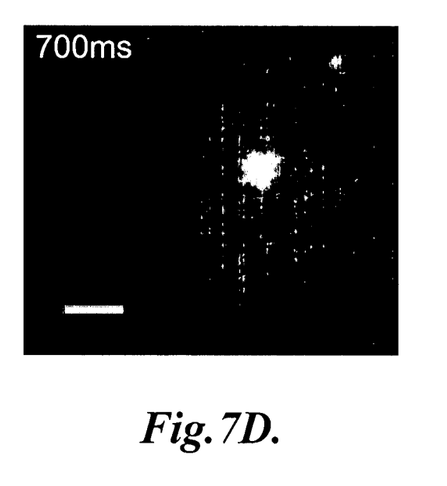
Figure 8A:
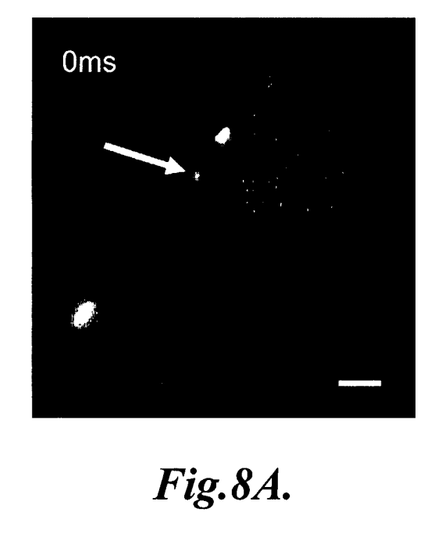
FIGS. 8A-8D illustrate the activation of a cell by one-photon photolysis of a capsule containing an active material.
Figure 8B:
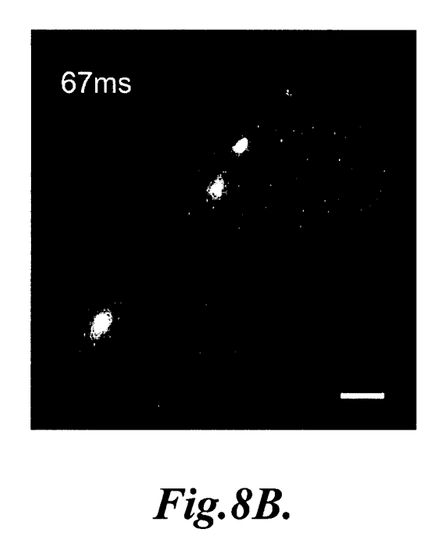
Figure 8C:
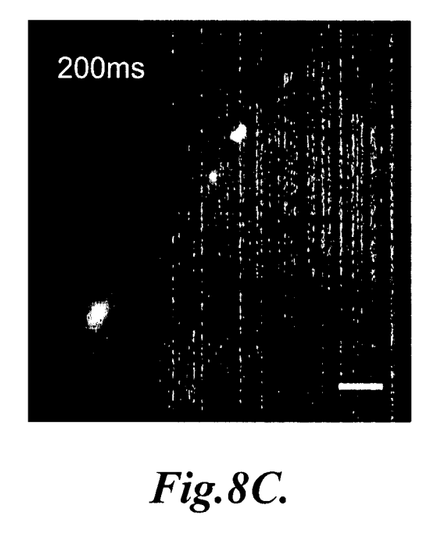
Figure 8D:
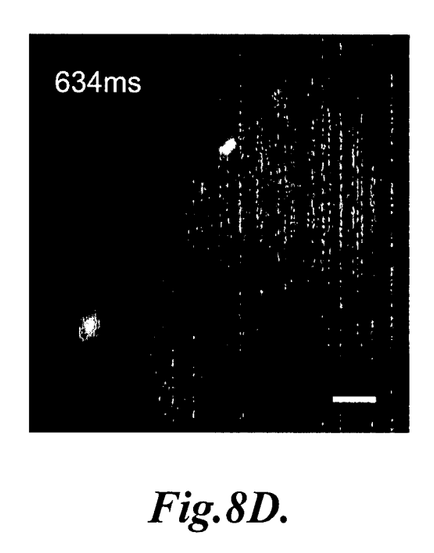

The wavelength of light used for photolysis of the shell material can be red-shifted so as to further decrease harmful effects on sensitive biological systems. This can be accomplished by using a two-photon process, as illustrated in FIGS. 7A-7D, depicting the two-photon photolysis of a single 400 nm vesicle at the near-IR wavelength of 710 nm. The vesicle was made from phosphatidyl choline doped with 3.3 mol % DiI (a two-photon sensitizer). Carbachol was used as the active material and CHO-M1 cells were targeted. FIGS. 7A-7D illustrate the result of a typical experiment, in which a single 400 nm vesicle (arrow), which was non-specifically attached to the single cell, was photolyzed. Prior to photolysis (time 0 ms; FIG. 7A), intracellular calcium level was low and the cell was not visible in fluorescence. After photolysis, using 710 nm light, and release of intra-vesicular carbachol, intracellular calcium increased and propagated across the cell (67 ms to 700 ms; FIGS. 7B-7D).

A peptide-cell interaction was facilitated by encapsulating a peptide as the active material and photolyzing the capsule near a target cell. FIGS. 8A-8D illustrate the one-photon photolysis of a single 400 nm vesicle at 645 nm light. The phosphatidyl choline vesicle was doped with 13 mol % DiD. The active material loaded into the capsule was 500 nM bradykinin, a small peptide, in order to activate a rat PC12 cell. The PC12 cells were grown on collagen-coated glass coverslips and given nerve growth factor to promote the formation of neurites. When bradykinin binds to the B2 receptor, hydrolysis of PtdInsP2 and formation of Ins(1,4,5)P3 occurs, resulting in the influx of intracellular $Ca^{2+}$, which is visualized with the calcium indicator dye Fluo3. FIGS. 8A-8D illustrate the activation of the cell by the active material, thus increasing the imaging fluorescent signal.

Example 4

Representative Applications

High-resolution imaging methods are available for visualizing the spatial distribution of proteins and receptors on the cell membrane, but these techniques do not provide functional information with regard to the activities of these proteins. The availability of spatially and temporally selective methods for probing cellular function and signaling dynamics is critical for understanding complex neuronal systems, and the capsule and methods of the invention may be used to facilitate such analysis.

The protection and controlled release of pharmacologically active substances is of great interest in drug development, and the capsule and methods of the invention are useful for both protecting and controllably releasing these substances. Another application of the invention is protection for compounds such as DNA, RNA, protein, or other molecules subject to biological degradation. After serving the purpose of protecting the molecule through its transit to the region of interest, the capsule then mediates release within the region of interest when exposed to a high flux of photons of the correct wavelength. The region of interest may be selected for the greatest therapeutic benefit or for scientific interest in determining the effect of the chemical.

Gene therapy has similar problems with vector toxicity and degradation. Anionic lipids have been shown to bind to DNA and facilitate (by unknown mechanisms) uptake into cells. In an exemplary use of the invention, anionic vesicle-DNA particles can be introduced into cells, tissue, a tumor, or anywhere a gene needs to be delivered, and the contents can be released specifically by pulsed light. This technique facilitates selective gene expression of (for example) suicide genes to cancerous cells or to perturb a single cell at the genetic level within a network of neuronal cells in culture.

In an exemplary application of the invention, the shell of the capsule or the interior of the capsule can be constructed to contain both the sensitizers for photolysis at a desired wavelength and also molecules that permit the detection and imaging of the capsules. For example, the capsule shell or interior may contain a type of molecules that fluoresces (or give rise to other optical signals) at a wavelength that is distinct from the wavelength used for photolysis, such that the capsules can be visualized using an appropriate imaging modality prior to, during, or after photolysis. Alternatively, an optical mechanism that is different than the one used for photolysis (e.g. one-photon for imaging and two-photon for photolysis) may be employed. The imaging and photolysis may be separately performed by using two different wavelength regions or two different optical mechanisms as described above. The imaging and photolysis may also be carried out using the same wavelength region and/or optical mechanism by being separately performed by varying laser power. For example, a low laser power can be used for imaging, but by increasing the laser power, the same laser can be used to photolyze the capsules. In this example, only one type of optically responsive molecule is needed, although the use of more than one type of molecule may confer other advantages.

The embodiments of the invention in which an exclusive property or privilege is claimed are defined as follows:

1. A capsule, comprising:
   (a) a shell, comprising a shell material;
   (b) an active material; and
   (c) a sensitizer having an absorbance wavelength from about 600 nm to about 1500 nm, wherein the sensitizer is configured to become excited to an excited state when irradiated with the absorbance wavelength, wherein the sensitizer is configured to initiate photolysis of the shell upon irradiation with light of the absorbance wavelength by transferring energy from the excited state to the shell, wherein the sensitizer comprises about 1 to about 20 mole percent of the shell, and wherein said photolysis disrupts the integrity of the shell to release the active material.

2. The capsule of claim 1, wherein the sensitizer is capable of one-, two-, or three-photon excitation.

3. The capsule of claim 1, wherein the sensitizer absorbance wavelength is a one-photon absorbance from about 600 nm to about 700 nm.

4. The capsule of claim 1, wherein the sensitizer absorbance wavelength is a two-photon absorbance from about 700 nm to about 1500 nm.

5. The capsule of claim 1, wherein the sensitizer is selected from the group consisting of 1,1'-dioctadecyl-3,3,3',3',-tetramethylindodicarbocyanine, 4-chlorobenzenesulfonate salt; 1,1'-dioctadecyl-3,3,3',3',-tetramethylindotricarbocyanine iodide; and 1,1'-dioctadecyl-3,3,3',3',-tetramethylindocarbocyanine perchlorate.

6. The capsule of claim 1, wherein the sensitizer is in the shell or attached to its surface.

7. The capsule of claim 1, wherein the sensitizer comprises about 10 to about 20 mole percent of the shell.

8. The capsule of claim 1, wherein the shell defines an interior volume that comprises the active material.

9. The capsule of claim 1, wherein the shell material is selected from the group consisting of a lipid, a polymer, and an inorganic material.

10. The capsule of claim 1, wherein the shell is a vesicle.

11. The capsule of claim 1, wherein the shell has a diameter from about 10 nm to about 1000 nm.

12. The capsule of claim 1, wherein the shell further comprises a targeting agent.

13. The capsule of claim 1, wherein the active material comprises two or more different active materials.

14. A capsule, comprising:
    (a) a shell, comprising a shell material;
    (b) an active material; and
    (c) a two-photon sensitizer having an absorbance wavelength from about 600 nm to about 1500 nm, wherein the sensitizer is configured to become excited to an excited state when irradiated with the absorbance wavelength, wherein the sensitizer is configured to initiate photolysis of the shell upon irradiation with light of the absorbance wavelength by transferring energy from the excited state to the shell, wherein the sensitizer comprises about 1 to about 20 mole percent of the shell, and wherein said photolysis disrupts the integrity of the shell to release the active material.

15. The capsule of claim 1, wherein disrupting the integrity of the shell comprises fracturing the shell.

16. The capsule of claim 14, wherein disrupting the integrity of the shell comprises fracturing the shell.

17. The capsule of claim 14, wherein the sensitizer comprises about 10 to about 20 mole percent of the shell.

18. The capsule of claim 14, wherein the shell is a vesicle.

19. A capsule comprising:
(a) a shell, comprising a shell material, wherein the shell is a vesicle;
(b) an active material; and
(c) a two-photon sensitizer having an absorbance wavelength from about 600 nm to about 1500 nm, wherein the sensitizer is configured to become excited to an excited state when irradiated with the absorbance wavelength, wherein the sensitizer is configured to initiate photolysis of the shell upon irradiation with light of the absorbance wavelength by transferring energy from the excited state to the shell, wherein the sensitizer comprises about 1 to about 20 mole percent of the shell, and wherein said photolysis disrupts the integrity of the shell to release the active material.

20. The capsule of claim 19, wherein the sensitizer comprises about 10 to about 20 mole percent of the shell.

* * * * *

UNITED STATES PATENT AND TRADEMARK OFFICE
CERTIFICATE OF CORRECTION

| | |
|---|---|
| PATENT NO. | : 8,697,121 B2 |
| APPLICATION NO. | : 11/925480 |
| DATED | : April 15, 2014 |
| INVENTOR(S) | : D. T. Chiu et al. |

Page 1 of 1

It is certified that error appears in the above-identified patent and that said Letters Patent is hereby corrected as shown below:

Title Page (73)     Assignee     "Unviersity of Washington, Seattle, WA (US)" should read --University of Washington, Seattle, WA (US)--

Signed and Sealed this
Sixteenth Day of September, 2014

Michelle K. Lee
*Deputy Director of the United States Patent and Trademark Office*